(12) United States Patent
Stickel

(10) Patent No.: US 9,063,069 B2
(45) Date of Patent: Jun. 23, 2015

(54) ULTRASOUND MEASUREMENT SYSTEM

(75) Inventor: Manfred Stickel, Wiesenbach (DE)

(73) Assignee: AMG Intellifast GmbH, Speyer (DE)

( * ) Notice: Subject to any disclaimer, the term of this patent is extended or adjusted under 35 U.S.C. 154(b) by 281 days.

(21) Appl. No.: 13/401,487

(22) Filed: Feb. 21, 2012

(65) Prior Publication Data

US 2012/0222485 A1    Sep. 6, 2012

Related U.S. Application Data

(60) Provisional application No. 61/444,330, filed on Feb. 18, 2011.

(51) Int. Cl.
| | |
|---|---|
| *G01N 29/00* | (2006.01) |
| *G01L 5/24* | (2006.01) |
| *G01N 29/24* | (2006.01) |
| *G01N 29/38* | (2006.01) |
| *G01H 1/00* | (2006.01) |
| *F16B 31/02* | (2006.01) |

(52) U.S. Cl.
CPC ............. *G01N 29/2475* (2013.01); *F16B 31/02* (2013.01); *G01L 5/246* (2013.01); *G01N 29/2481* (2013.01); *G01N 29/38* (2013.01); *G01N 2291/044* (2013.01); *G01N 2291/2691* (2013.01); *G01H 1/00* (2013.01)

(58) Field of Classification Search
USPC ................... 73/596–598, 629–632, 587–588, 73/579–582, 761, 776, 778
See application file for complete search history.

(56) References Cited

U.S. PATENT DOCUMENTS

| | | | | | |
|---|---|---|---|---|---|
| 4,014,208 | A | * | 3/1977 | Moore et al. | 73/629 |
| 4,062,227 | A | * | 12/1977 | Heyman | 73/630 |
| 4,333,351 | A | * | 6/1982 | Bickford | 73/761 |
| 4,899,591 | A | * | 2/1990 | Kibblewhite | 73/761 |
| 5,220,839 | A | * | 6/1993 | Kibblewhite | 73/761 |
| 5,237,516 | A | * | 8/1993 | Heyman | 702/42 |
| 5,948,984 | A | * | 9/1999 | Hedberg | 73/588 |
| 5,970,798 | A | * | 10/1999 | Gleman et al. | 73/761 |
| 6,186,010 | B1 | * | 2/2001 | Eguchi et al. | 73/761 |
| 6,358,051 | B2 | * | 3/2002 | Lang et al. | 433/173 |
| 7,360,435 | B2 | * | 4/2008 | Nassar et al. | 73/761 |
| 7,412,898 | B1 | * | 8/2008 | Smith et al. | 73/761 |
| 7,467,556 | B2 | * | 12/2008 | Kibblewhite et al. | 73/761 |
| 7,975,555 | B2 | * | 7/2011 | Zhuang et al. | 73/778 |
| 8,177,464 | B2 | * | 5/2012 | Zendehroud et al. | 411/8 |
| 8,511,175 | B2 | * | 8/2013 | Hoering et al. | 73/776 |
| 2006/0130590 | A1 | * | 6/2006 | Kibblewhite et al. | 73/761 |

(Continued)

FOREIGN PATENT DOCUMENTS

| | | |
|---|---|---|
| DE | 42 24 035 A1 | 1/1994 |
| DE | 42 32 254 A1 | 4/1994 |

(Continued)

*Primary Examiner* — Helen Kwok

(57) ABSTRACT

An ultrasound measurement system and a method for carrying out ultrasound measurements is provided that includes a data acquisition unit and a transducer for coupling an ultrasound pulse into a connecting element and for extracting an ultrasound pulse echo from the connecting element. The ultrasound measurement system proposed according to the invention comprises the data acquisition unit which has a combination of analog and digital electronics for excitation and driving of the transducer. This is separated from a data processing unit and is in contact therewith via a wired or wireless connection.

11 Claims, 2 Drawing Sheets

(56) References Cited

U.S. PATENT DOCUMENTS

2010/0050778 A1* 3/2010 Herley et al. .................. 73/761
2011/0146412 A1 6/2011 Hoering et al.

FOREIGN PATENT DOCUMENTS

| DE | 10 2004 038 638 | 6/2006 |
| DE | 10 2009 060 441 A1 | 6/2011 |

* cited by examiner

ULTRASOUND MEASUREMENT SYSTEM

This nonprovisional application claims priority to U.S. Provisional Application No. 61/444,330, which was filed on Feb. 18, 2011, and which is herein incorporated by reference.

BACKGROUND OF THE INVENTION

1. Field of the Invention

The present invention relates to an ultrasound measurement system which comprises an ultrasound transducer and permits accurate time-of-flight measurements of ultrasound pulses in connecting elements which are under mechanical stress, for example screws, bolts, rivets or the like.

2. Description of the Background Art

DE 42 25 035 A1 and DE 42 32 254 A1 disclose ultrasound testing methods. DE 10 2004 038 638 relates to a connecting component, in the head or foot region of which there is an ultrasound sensor whose structure is formed as a layer structure.

DE 10 2009 060 441 A1, which corresponds to US2011/0146412, and which is incorporated herein by reference, relates to a sensor element. A connecting component comprises an integrated ultrasound sensor for analyzing the mechanical stress distribution, in particular for determining the prestress force of the connecting component, the ultrasound sensor having at least a two-layered structure comprising an electrode layer and at least one layer of a material having piezoelectric properties. The electrode layer and the layer of a material having piezoelectric properties are vapor deposited, in particular sputtered, on at least one freely accessible end of the connecting part, structures being formed in the electrode layer by generating laser-ablated regions.

The most important field of ultrasound measurement methods is to be seen in the examination of mechanical stress statuses, in particular measurement of the prestress force in connecting elements of different designs. A further very wide field is the "health monitoring" of connecting elements and components which are exposed to dynamic loads. The basis of these measurements includes the excitation, propagation and detection of mechanical ultrasound waves in the materials to be examined, which pass through the regions of the components which are under load or stress while changing their properties in a characterizable way. Especially in the case of force measurement, the difference in the times of flight of an ultrasound pulse between a connecting element which is under mechanical stress and an unloaded reference status is determined. By the mechanical stress, both a lengthening of the connecting element is induced and the speed of sound in the material is reduced. An increase in the sound time of flight can therefore be measured, which can in turn be converted into forces by means of empirical calibration parameters.

The aforementioned methods for equipping connecting elements with adhesively bonded or sputtered transducers places a converter, which converts electrical signals and waveforms into mechanical ultrasound pulses and vice versa, directly on the connecting element. For exciting the transducer and registering the echo, a combination of digital and analog electronics is necessary, which are connected to the transducer by means of cables. For data analysis, data storage and representation of the measurement results, a computer integrated into the measurement unit is used. The pulse transmission and echo reception electronics are applied together with the evaluation computer in a common housing or slot-in rack. In order to avoid interference of the measurement signals and to limit the signal attenuation, the integrated measurement unit itself must be placed in the vicinity of the measurement position.

SUMMARY OF THE INVENTION

It is therefore an object of the present invention to provide an ultrasound measurement system which allows examination of the mechanical stress status and the internal structure of polycrystalline materials by ultrasound transducers according to the principle of the ultrasound pulse echo method.

In particular, it is an object of the present invention to reliably permit determination of the prestress force in connecting elements of different designs, for example screws, bolts or rivets.

In order to measure the stress statuses in the connecting elements, however, merely the analog/digital components of the pulse transmission and echo reception electronics are required at the position of the measurement, since the analog signals involved cannot be transmitted wirelessly from and to the transducer. After digitization of the echo signals, all the other method steps may be carried out both spatially and temporally separately from the position and time of the excitation of the transducer. Separation, proposed according to the invention, of the analog-digital pulse transmission and echo reception electronics from the data analysis and storage unit downstream is advantageous in cases when there are great spatial restrictions at the measurement position and no measurement electronics can be installed, when the measurement position is not constantly accessible and the status is intended to be monitored continuously over time, or when manual measurements are intended to be carried out occasionally or in an inspection mode with the least possible installation size.

In particular, with modern wireless transmission methods, digital data can be transmitted without interference and losses to an analysis system with corresponding evaluation software, which can run free from special hardware on any suitable computer system and can therefore be adapted easily to extended requirements in terms of the analysis methods or can utilize improved computer technologies (for example faster CPUs) for example for higher measurement rates. Restriction of the user to particular hardware and measuring equipment provision is substantially reduced. Separate development of the analog-digital pulse transmission and echo reception electronics and their purely information-technological connection to a corresponding industry-compatible computer system reduces the turnaround time for technical modifications.

If the connecting element is permanently equipped with the aforementioned analog-digital pulse transmission and echo reception electronics, the previously passive screw provided with a transducer becomes, with the electronics, an active element of a connection which can act as a physical sensor e.g. for pressure/temperature and can monitor itself. One advance is integration of the transducer/electronics combination into the screw already during its manufacture, in which case the active screw can enter into communication with its environment, and either be actively interrogated or autonomously send all the necessary data about its status, without a constant connection to a receiver of the data necessarily being required.

According to the solution proposed according to an embodiment of the invention, the difference in the times of flight of an ultrasound pulse between a connecting element which is under mechanical stress and an unloaded reference status is determined, which difference can be converted into forces by means of empirical calibration parameters. The time of flight of an ultrasound pulse in a material is in turn given by the length of a connecting element together with the speed of sound, the transmitted pulse being reflected at the opposite end from the transmitter. The force measurement method is based on the physical principles of the length change of a connecting element under mechanical stress and the associated reduction of the propagation speed of a wave. Both mechanisms lead to an increase in the time of flight of an ultrasound pulse in a connecting element in the installed, i.e. loaded state.

For generating an ultrasound pulse into a connecting element, a converter is required which converts electrical signal forms into corresponding mechanical waveforms on transmission of the pulse and conversely converts these back into an analog electrical signal on reception of the echo. Such ultrasound transducers exist in a very wide variety of designs and have a very wide variety of transduction characteristics. The thin-film piezo transducer applied in a high vacuum according to DE 10 2009 060 441 A1 may be mentioned in particular, which has a very broadband transduction characteristic and delivers relatively weak echo signals. In contrast to this, for example, there are conventional adhesively bonded piezo disk transducers, which are very narrow-band and are capable of delivering correspondingly stronger ultrasound echo signals.

The ultrasound measurement system proposed according to the invention uses these different embodiments, i.e. different transduction characteristics of the transducers, in close combination with digital hardware, and takes care of the necessary organization of the measurement cycle which comprises waveform definition, transmission of the ultrasound pulse, waiting a previously specified time period until return of the echo, and digitization and forwarding of the latter with additional data.

An analog signal component directly connected thereto undertakes the task of converting the transmission and reception pulses between the analog and digital signal form as well as filtering and amplification of the signals of the ultrasound echo, which are very weak particularly in the case of thin-film transducers.

According to the solution proposed according to an embodiment of the invention, only the electronics absolutely necessary for excitation of the transducer and detection of the echo are placed at the position of the measurement. The information collected is transmitted in digital form by means of a cable or wirelessly to the corresponding other components of the measurement system, which may be spatially separated from the position of the measurement, while the evaluation of the transmitted information may be carried out both spatially and temporally separately from the data acquisition.

Besides individual measurements with a corresponding external trigger, repeated or automatic measurement series may also be controlled by the ultrasound measurement system, to the extent of substantially autonomous execution of predefined measurement cycles, connection to the external data analysis and control system not always needing to be ensured.

It is advantageous to apply the data acquisition unit of the ultrasound measurement system proposed according to the invention as close as possible to the position of the measurements. However, since the installation situation or accessibility do not always allow this, the analog electrical signal of the transmission pulse and the signal of the echo may be delivered through cables of variable length. Owing to the finite signal speed in the cable, this will entail a non-negligible contribution to the overall time of flight of the pulse, which needs to be separately determined and subtracted in order to produce the pure ultrasound time of flight of the ultrasound pulse in the connecting element. In combination with the hardware, the ultrasound measurement system must provide the necessary method for measuring this so-called cable time of flight directly or for receiving an externally measured cable time of flight existing in the form of a numerical value and applying it correctly for the ultrasound time-of-flight measurements.

Advantageously, for universal use in a wide variety of application fields, the data acquisition unit of the ultrasound measurement system may be integrated into a transportably held housing. This preferably comprises a combination of specially developed analog electronics in combination with a digital part for control. Owing to the embodiment of separating the data acquisition unit from the data evaluation unit, as proposed according to the invention, above all the handling is substantially more favorable because of the possible miniaturization, and so are the force measurement rate and electricity consumption. The data acquisition unit can be used substantially more flexibly and optionally also satisfy extended guidelines, in particular explosion safety requirements. Strict separation of the measurement of data and the data processing is carried out in the ultrasound measurement system proposed according to the invention, which provides the possibility of operating a plurality of data acquisition units from only one data evaluation station (for example via Ethernet or WLAN). The data acquisition unit remains invisible to the user, operates almost entirely without maintenance and, owing to its very low degree of complexity, can be optimized for the actual measurement process—especially in terms of speed.

In summary, the data acquisition unit of the ultrasound measurement system proposed according to the invention, with strict separation of the data acquisition and data processing, is distinguished by very great transparency in terms of the user. The measurement system is extremely low-maintenance since there are only a few configuration parameters. Furthermore, there is a straightforward possibility of updating via Ethernet or WLAN. The data acquisition unit compiles a detailed error report analysis and is distinguished by a high data acquisition rate and low power consumption, together with a high force measurement rate. Furthermore, the data acquisition unit of the ultrasound measurement system proposed according to the invention is extremely easy to handle, which is attributable not least to a small and compact housing.

In the solution proposed according to the invention for an ultrasound measurement system, the data acquisition unit comprises the connection to the ultrasound transducer as a part operating in analog, while the digital component is used for data processing and organization of the data acquisition unit, and furthermore constitutes the interface to the user or operator.

The part of the hardware component operating in analog may be divided between the two signal paths of the transmission pulse from the data acquisition unit to the transducer and of the echo signal from the transducer to the data acquisition unit. Outside the data acquisition unit, the two signal paths necessarily use the same signal cable, in particular one formed as a coaxial cable. The outlay for connecting the data acquisition unit to the transducer is thereby limited to the minimum absolutely necessary. Particular demands are placed especially on the generation and transmission of the waveforms to and from the transducer. The large dynamic range of the echo signals to be expected in the waveform transmission is determined by various transducer designs, the very high (for measuring such small forces) accuracy requirements for the time-of-flight measurement and the sometimes very strong effects of the material travelled through.

It is therefore desirable to carry out the signal transmission as far as possible without noise, with a high gain and undistorted within the excited bandwidth of the transducer, frequency-independently, phase-stably, substantially without time ambiguities and with a high absolute time resolution.

The digital hardware component is used for temporal control and regulation of the analog hardware component and of the ultrasound time-of-flight measurement cycles as a whole. All the parameters necessary for defining the pulse waveform and for the process control are available at the time of a measurement. This is ensured by the software of this component. The user of the ultrasound measurement system proposed according to the invention is in communication with this component, in order to initiate ultrasound time-of-flight measurements and obtain their results in the form of digitized echoes and further information. For further processing of the measurements, export and transfer of the digitized echo signals, together with all the other parameters relevant to the measurement, is provided to a downstream data processing unit spatially separated from the data acquisition unit.

Since temperature changes also alter the length of connecting elements and therefore ultrasound times of flight, separate synchronized measurement of the temperature during the propagation of the ultrasound pulse is necessary. This is done by means of a high-accuracy temperature-sensitive resistor element, for example a Pt100 measurement sensor.

Although the data acquisition unit should be applied as close as possible to the position of the time-of-flight measurements, this optimal situation cannot be selected in all cases. There is therefore a need to deliver the analog electrical signal of the transmission pulse and the signal of the echo through cables of variable length. Owing to the finite signal speed inside the cable, this will entail a non-negligible contribution to the overall time of flight of the ultrasound pulse, which needs to be separately determined and subtracted in order to produce the pure ultrasound time of flight in the connecting element. The digital hardware component provides a way of determining the time of flight of the electrical signal in the connecting cable directly and exporting it via the user interface, so that it can be subtracted from the time of flight measured overall.

For the two measurement quantities to be acquired, namely time of flight and temperature, a high-accuracy quartz oscillator and external temperature sensors are used on the hardware side. In turn, these must themselves be calibrated at regular time intervals with corresponding reference standards, in order to ensure the functionality and correctness of the measurement results. To this end, corresponding signal inputs are provided.

In order to carry out an ultrasound cycle, the ultrasound measurement system proposed according to the invention performs the following tasks with a combination of hardware components operating in digital and operating in analog:

A complex temporally limited analog electrical pulse waveform is generated. Variable amplification of the generated analog signal is possible for exciting ultrasound transducers of different designs. The generated electrical waveform is transmitted to the position of the transducer. After the ultrasound pulse has been transmitted, the output signal chain is switched off to avoid unnecessary interference in the reception signal chain. After a variable predetermined time period has elapsed, ultrasound echoes are detected. At the same time, the temperature of the connecting element is determined during the ultrasound pulse propagation in the material of the component to be measured.

Bandpass filtering and amplification of the very weak echo signals of the transducer, which is now operating as a receiver, are then carried out. This is followed by digitization of the amplified input signal over a predetermined time range after transmission of the pulse, and optionally averaging thereof over a number of echoes in order to increase the signal-to-noise ratio.

A complete time series, i.e. a measurement cycle together with further complementary data, is subsequently forwarded via a data transfer channel (for example Ethernet) to a system of the PC type for further data analysis.

Further scope of applicability of the present invention will become apparent from the detailed description given hereinafter. However, it should be understood that the detailed description and specific examples, while indicating embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
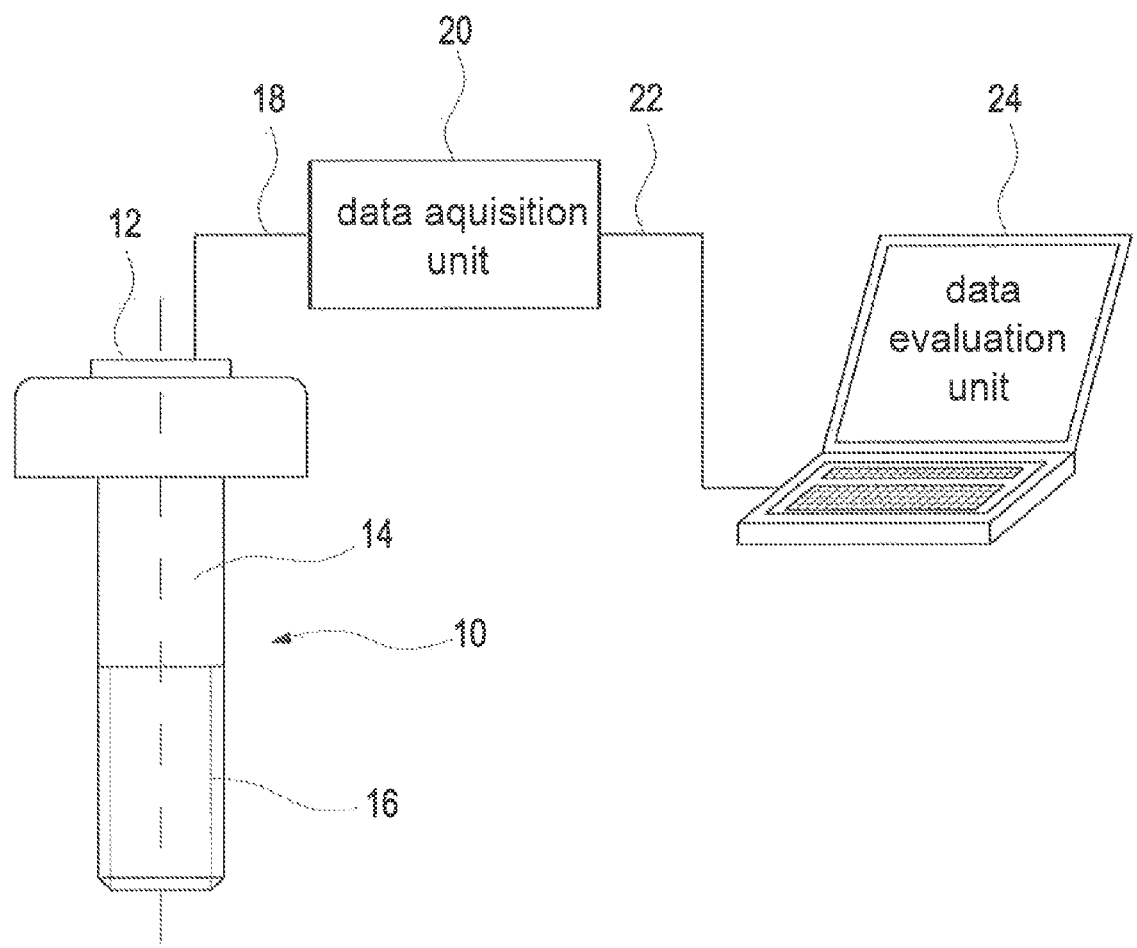
FIG. 1 shows a schematic structure of the ultrasound measurement system proposed according to an embodiment of the invention.

The representation according to FIG. 1 shows a schematic representation of the ultrasound measurement system proposed according to the invention.

The representation according to FIG. 1 shows a connecting element 10 which, in the representation according to FIG. 1, is a screw. As an alternative to this, the connecting element 10 may also be a rivet, a bolt or another connecting component. FIG. 1 furthermore shows that a transducer 12 is arranged on the head of the connecting element 10. The transducer 12 may be one which is formed in thin-film technology or another commercially available ultrasound transducer 12.

The connecting element 10 comprises a shaft 14. The shaft 14 of the connecting element 10—formed as a screw—is followed by a section comprising a screw thread 16. Via the transducer 12, the connecting element 10 according to the representation of FIG. 1 is connected to a data acquisition unit 20 comprising an integrated analog/digital converter.

The cable connection 18 between the transducer 12 and the data acquisition unit 20 is preferably provided by a coaxial cable. The cable connection 18 between the data acquisition unit 20 and the transducer 12 is not always necessary. If the installation conditions of the connecting element 10 so permit, the data acquisition unit 20 may be placed directly on the upper side of the transducer 12. In this way, the electrical coupling of the transducer 12 may take place directly at the data acquisition unit 20. If the installation conditions of the connecting element 10 do not permit this, on the other hand, it is optionally possible to connect the transducer 12 on the upper side of the connecting element 10 to a measurement module 20 via the cable connection 18 and thereby deliver the excitation signals to the transducer 12 and transmit the received echoes to the data acquisition unit 20 via the cable connection 18, configured in particular as a coaxial cable.

Via a wired or wireless connection 22, which may for example be Ethernet or WLAN or the like, the data acquisition unit 20 is in turn connected to a system allowing data processing, in particular a PC, which is used for evaluation of the data (indicated in the figure by the data evaluation unit 24).

Figure 2:
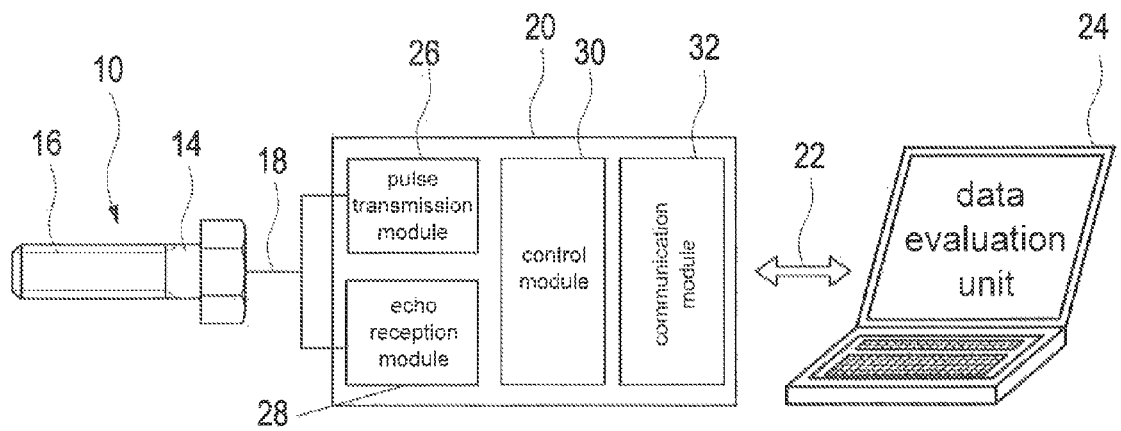
FIG. 2 shows a representation of the components of the data acquisition unit.

Components of the data acquisition unit can be seen in the representation according to FIG. 2.

As shown by FIG. 2, the data acquisition unit 20 is connected via the cable connection 18 to the connecting element 10, here formed as a screw. The data acquisition unit 20 comprises a pulse transmission module 26 by which an ultrasound pulse is introduced via the cable connection 18 and the transducer (not shown in FIG. 2) into the connecting element 10. The data acquisition unit 20 furthermore comprises an echo reception module 28 which—likewise via the cable connection 18—receives the echo of the ultrasound pulse, transmitted by the pulse transmission module 26, from the connecting element 10 via the transducer (not shown in FIG. 2). According to the schematic representation according to FIG. 2, the data acquisition unit 20 furthermore contains a control module 30 and a communication module 32. By means of the communication module 32, the correspondingly processed data are communicated via the wireless connection 22 to the data evaluation unit 24. The control module 30 undertakes the logical and temporal process control of all the components involved in the measurement process. In particular, correction of the time of flight of the ultrasound pulse in the connecting element 10 by the time-of-flight component due to the time of flight in the cable connection 18 is carried out in the control module 30. Temperature compensation of the measured ultrasound pulse time of flight through the connecting element 10 is furthermore carried out in the control module 30.

The temperature effect on the ultrasound echo time of flight inside the connecting component 10 formed as a screw is furthermore taken into account in the control module 30, since the latter is equipped with corresponding algorithmic intelligence. Data correspondingly corrected to the pure ultrasound signal time of flight in the connecting element 10 are communicated via the communication module 32 and the wired or wireless connection 22 to the data evaluation unit 24—here indicated by a laptop.

Figure 3:
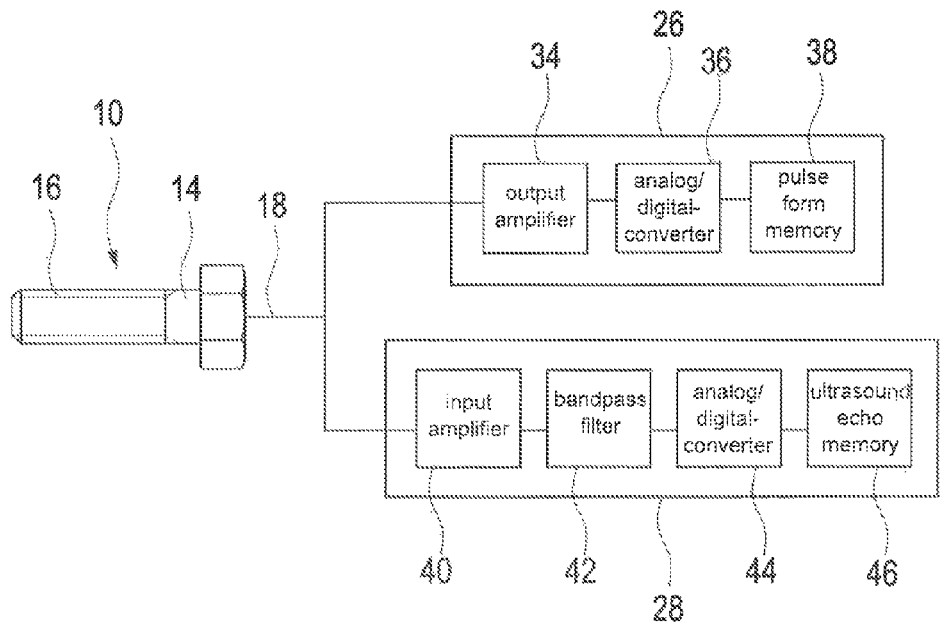
FIG. 3 shows a detailed representation of the components which are contained in a pulse transmission module and an echo reception module of the data acquisition unit.

Individual components of the pulse transmission module represented in FIG. 2, and of the echo reception module of the data acquisition unit, as represented in FIG. 2, can be seen in the representation according to FIG. 3.

FIG. 3 shows that, in a similar way to the representation according to FIG. 2, the pulse transmission module 26 is connected via the cable connection 18 to the connecting component 10, here formed as a screw, with the interconnection of a transducer (not shown in FIG. 3). The pulse transmission module 26 comprises an output amplifier, by which the ultrasound pulse is coupled into the connecting element 10 by means of the cable connection 18. The pulse transmission module 26 according to the representation in FIG. 3 furthermore comprises a pulse form memory 38, in which various ultrasound pulse forms are represented in digital form. Provided between the pulse form memory 38 and the output amplifier 34, there is a digital/analog converter 36 that converts the ultrasound pulses, which are provided in digital form and are stored in the pulse form memory 38, into corresponding analog signals which are coupled by means of the output amplifier 34 into the cable connection 18 to the transducer 12 of the connecting component 10.

The echo reception module 28 contained in the data acquisition unit 20 comprises, on the input side, an input amplifier 40 by means of which the ultrasound echoes obtained from the connecting component 10 via the transducer 12 (not shown in FIG. 3) and the cable connection 18 are amplified. Downstream of the input amplifier 40 of the echo reception module 28, there is a bandpass filter 42; downstream of this there is in turn an analog/digital converter 44. By means of the analog/digital converter 44, the analog echo signals are converted into digital signals which are stored in an ultrasound echo memory 46 of the echo reception module 28 of the data acquisition unit 20.

FIGS. 1 and 2 show that the connection 22 is formed, for example, as a wireless connection between the data acquisition unit 20 and the data evaluation unit 24. For example, a WLAN connection may be envisaged as the wireless connection. As an alternative to this, the connection 22 may also be formed so as to be wired and, for example, configured as an Ethernet connection.

The ultrasound measurement system proposed according to the invention, as described above with the aid of FIGS. 1 to 3, may also be used in a further advantageous application to carry out multiple screwing, for example on a flange. In the scope of multiple screwing, for example, four, six or another number of connecting elements 10, for example screws, are screwed onto a hub, for example on a wind generator motor and on a hub of a wind generator motor. To this end, a plurality of simultaneously operated tightening tools will generally be used, in each of which a data acquisition unit 20 as described above is integrated, the overall resulting system being operated for a plurality of tightening tools, each with integrated data acquisition units per se, by means of a control loop so that multiple screwing can be achieved simultaneously on all the connecting elements 10 with defined prestress forces.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. An ultrasound measurement system comprising:
a data acquisition unit;
a transducer configured to couple an ultrasound pulse into a connecting element and configured to extract an ultrasound pulse echo from the connecting element;
wherein the data acquisition unit is structurally separated from a data processing unit and is connected thereto by a wired or wireless connection and wherein the data acquisition unit comprises a control module which is adapted to compensate for a cable time of flight of the ultrasound pulse prior to the conversion by the transducer.

2. The ultrasound measurement system according to claim 1, wherein the data acquisition unit has analog and digital components necessary for excitation of the transducer and is configured for echo reception at the measurement position, and has a structural form which is as small as possible.

3. The ultrasound measurement system according to claim 1, wherein data processing in the data processing unit is carried out spatially and temporally separately from an excitation of the transducer and an echo reception.

4. The ultrasound measurement system according to claim 1, wherein a plurality of independent data acquisition units are connected to a single central data processing unit by connections.

5. The ultrasound measurement system according to claim 1, wherein, after appropriate configuration, the data acquisition unit autonomously establishes a status of the connecting element, and forwards the information, automatically at regular or irregular time intervals.

6. The ultrasound measurement system according to claim 1, wherein the data acquisition unit is combined as part of a manual inspection device together with a further component for identification of the connecting element for simplified and error-free checking and monitoring of a stress status of connecting elements.

7. The ultrasound measurement system according to claim 1, wherein the data acquisition unit is integrated directly into the connecting element, so that the connecting element with a drivable transducer for ultrasound measurement becomes an active connecting element which autonomously determines the status own status and reports the status to a data evaluation unit.

8. The ultrasound measurement system according to claim 1, wherein the data acquisition unit is integrated into tightening tools or is connected thereto in a function-enhancing way, so as to carry out screwing of connecting elements under ultrasound control with a defined prestress force.

9. The ultrasound measurement system according to claim 1, comprising a plurality of simultaneously operating tightening tools and a plurality of data acquisition units, wherein the data acquisition unit is respectively integrated into each tightening tool, and wherein the system thus obtained is controlled by means of a control loop so that each tightening tool carries out screwing with a defined prestress force on a connecting element.

10. Use of the ultrasound measurement system according to claim 1, wherein the system is used for monitoring a lifetime of components.

11. A method for carrying out ultrasound measurements in connecting elements with an ultrasound measurement system according to claim 1, the method comprising:
   generating a complex temporally limited analog electrical pulse waveform,
   transmitting the generated pulse waveform to a position of the transducer
   switching off an output signal chain after transmission of the pulse in order to avoid unnecessary interference in a reception signal chain,
   detecting an ultrasound echo after a variable predetermined time period,
   determining a temperature of the connecting element at the time of an ultrasound pulse propagation in the connecting element,
   bandpass filtering and amplification of echo signals of the transducer operating as a receiver,
   digitization of an amplified input signal over a predetermined time range after transmission of the pulse and/or averaging thereof over a number of echoes,
   correction of a time of flight of the pulse due to a cable time of flight, and
   forwarding a complete time series together with further complementary data via wired or wireless connections to a data evaluation unit.

* * * * *